US00PP25077P3

(12) United States Plant Patent
Bourne

(10) Patent No.: US PP25,077 P3
(45) Date of Patent: Nov. 18, 2014

(54) ***DIANTHUS* PLANT NAMED 'WP11 TYR04'**

(50) Latin Name: *Dianthus×hybrida*
Varietal Denomination: WP11 TYR04

(71) Applicant: Planthaven International, Inc., Santa Barbara, CA (US)

(72) Inventor: Carolyn Grace Bourne, Dawlish (GB)

(73) Assignee: Carolyn Grace Bourne (GB)

( * ) Notice: Subject to any disclaimer, the term of this patent is extended or adjusted under 35 U.S.C. 154(b) by 143 days.

(21) Appl. No.: 13/694,993

(22) Filed: Jan. 23, 2013

(65) Prior Publication Data

US 2013/0232651 P1 Sep. 5, 2013

(30) Foreign Application Priority Data

Feb. 3, 2012 (QZ) ..... PBR 20120271

(51) Int. Cl.
*A01H 5/00* (2006.01)

(52) U.S. Cl.
USPC ..... Plt./272

(58) Field of Classification Search
USPC ..... Plt./272, 273
See application file for complete search history.

*Primary Examiner* — Kent L Bell

(74) *Attorney, Agent, or Firm* — Barbara Campbell; Cochran Freund & Young LLC

(57) ABSTRACT

A new cultivar of *Dianthus* plant named 'WP11 TYR04' which is characterized by a compact mounding habit, blue-green foliage, fragrant single flowers that are strongly patterned cherry red with white-pink markings and a deep cherry eye, and ruffled petal edges. In combination, these characteristics set 'WP11 TYR04' apart from all other existing varieties of *Dianthus* known to the inventor.

2 Drawing Sheets

Genus: *Dianthus.*
Species: ×*hybrida.*
Denomination: 'WP11 TYR04'.

BACKGROUND OF THE INVENTION

This application claims the benefit of priority under 35 U.S.C. 119(f) of the earlier application for European Community Plant Variety Rights which was filed for the instant plant variety on Feb. 3, 2012, Application Number 2012/0271.

The present invention relates to a new and distinct cultivar of hardy garden pink, that is grown for use as a flowering plant for pots and containers and for planting in the garden and landscape. The new cultivar is known botanically as *Dianthus×hybrida* and will be referred to hereinafter by the cultivar name 'WP11 TYR04'.

'WP11 TYR04' is a complex hybrid plant that is the product of a long term breeding program conducted by the inventor in a cultivated area of Houndspool, Dawlish, Devon, United Kingdom. The inventor selected 'WP11TYR04' in 2004 for its strongly patterned cherry red, white-pink single flowers with a deep cherry eye, ruffled petal edges, moderate fragrance and blue-green foliage.

'WP11 TYR04' arose and was selected as a seedling which resulted from the open pollination of an existing selection of *Dianthus* from the inventor's breeding program, namely *Dianthus* code name 'Zora' (unpatented and unreleased) as the female parent plant, by an unknown selection from the breeding program as male parent plant. The male parent was growing within the inventor's stock of breeding lines.

'WP11 TYR04' is distinguishable from the female parent as follows: Whereas the flower of 'WP11 TYR04'is single and strongly patterned cherry red, white-pink with a deep cherry eye, the flower of 'Zora' is semi-double and shell pink in color. The flowers of 'Zora' are smaller than the flowers of 'WP11 TYR04'. In addition, the foliage of the 'Zora' is green in color, whereas the foliage of 'WP11 TYR04' is blue-green in color.

The identity of the male parent is unknown and therefore a comparison is not possible.

The variety of *Dianthus* which is considered by the inventor to most closely resemble 'WP11 TYR04' is the inventor's variety *Dianthus* 'Starburst' (U.S. Plant Pat. No. 21,162). The flowers of 'Starburst' have a similar blotching pattern on their petals, but the patterns and colors are different. 'WP11 TYR04' has a radiating pattern of white-pink on a background of cherry red with pronounced white stamens. 'Starburst' has a more subdued pattern of pink-white on a background of cherry red with distinctive pointed petals and the stamens are covered by the petals. Additionally the flowers of 'Starburst' are semi to fully double, while 'WP11 TYR04' bears single blooms with ruffled petal edges.

Asexual reproduction of 'WP11 TYR04' was first accomplished by the inventor in 2004 in a cultivated area of Houndspool, United Kingdom. The method of asexual propagation used was vegetative cuttings. The inventor has determined that 'WP11 TYR04' is stable and reproduces true to type in successive generations of asexual propagation.

SUMMARY OF THE INVENTION

The following traits have been repeatedly observed and represent the characteristics of the new *Dianthus* cultivar 'WP11 TYR04'. These traits in combination distinguish this cultivar from all other commercial varieties known to the inventor. 'WP11 TYR04' has not been tested under all possible conditions and phenotypic differences may be observed with variations in environmental, climatic and cultural conditions, however, without any variance in genotype.

1. 'WP11 TYR04' exhibits a compact mounding habit.
2. 'WP11 TYR04' bears single flowers that are cherry red with white-pink markings and a deep cherry eye.
3. 'WP11 TYR04' exhibits petals that are deeply ruffled.
4. 'WP11 TYR04' blooms from Mid-April through October.
5. The flowers of 'WP11 TYR04' are moderately fragrant
6. 'WP11 TYR04' exhibits glaucous, blue-green foliage.
7. At maturity, the height of the foliage mound of 'WP11 TYR04' is 20 cm, and the width is 22 cm.
8. 'WP11 TYR04' is perennial and is hardy at least to −15° C.
9. 'WP11 TYR04' is suitable for use as a flowering plant in pots and containers.

BRIEF DESCRIPTION OF THE DRAWINGS

The accompanying color drawings illustrate the overall appearance of the new *Dianthus* variety 'WP11 TYR04' showing colors as true as it is reasonably possible to obtain in colored reproductions of this type. Colors in the drawings may differ from the color values cited in the detailed botanical description, which accurately describe the actual colors of the new variety 'WP11 TYR04'.

The drawing labeled as FIG. 1 depicts an entire flowering plant of 'WP11 TYR04'.

Figure 1:
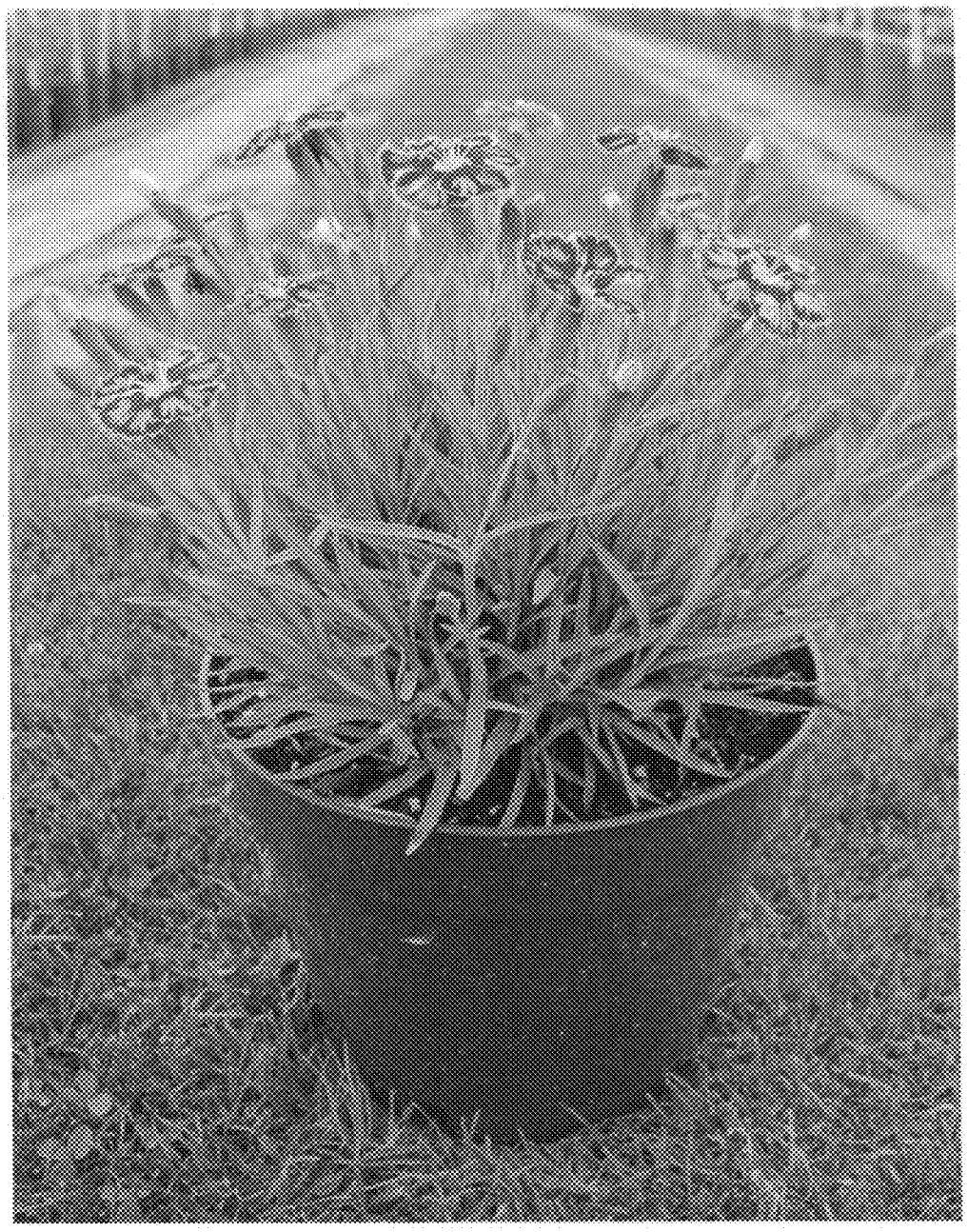
Figure 2:
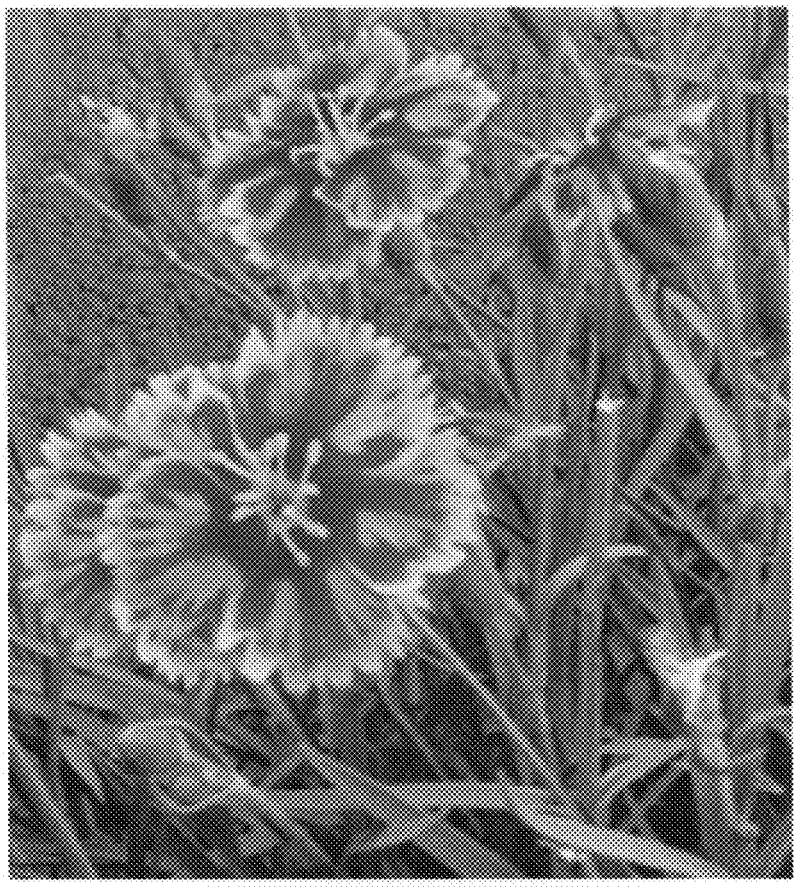

The drawing labeled as FIG. 2 depicts a close-up view of the flower of 'WP11 TYR04'.

All drawings were made from 9 months old plants which have been grown in 1.5-litre containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP11 TYR04'. Data was collected from plants grown in 1.5-litre containers under an unheated glasshouse in Houndspool, United Kingdom in July. The color determinations are in accordance with the 2001 edition of The Royal Horticultural Society Colour Chart of The Royal Horticultural Society, London, England, except where general color terms of ordinary dictionary significance are used. No chemicals were used to treat the plants. Growing conditions are typical to other *Dianthus*.

Botanical classification: *Dianthus 'WP*11 TYR04'.

Species: ×*hybrida* L.

Common name: Garden pink.

Commercial classification: *Dianthus* hybrid.

Type: Perennial.

Use: Used as a flowering plant for pots, containers and planting in the garden or landscape.

Parentage: 'WP11 TYR04' is a complex hybrid plant that resulted from the open pollination of *Dianthus* seedlings.

*Female parent plant.*—*Dianthus* 'Zora' (unpatented).

*Male parent plant.*—Unknown.

Plant description:

*Bloom period.*—Mid-April to October.

*Plant habit.*—Compact mounding habit.

*Plant height.*—20 cm in overall height, including flower canopy.

*Plant width.*—22 cm in width.

*Plant hardiness.*—Hardy to minus 15° Centigrade.

*Root system.*—Fine fibrous roots.

*Propagation.*—Propagation is accomplished using vegetative stem cuttings.

*Cultural requirements.*—Plant in full sun, well-drained and moderately fertile soil and keep well fertilized and watered.

*Diseases and pests.*—No particular resistance or susceptibility to known *Dianthus* pests and diseases are known to the inventor.

*Time to root cuttings.*—10-14 days are required to produce roots on a vegetative cutting at the recommended temperatures.

*Recommended temperature for rooting.*—A minimum of 15° C. air temperature and 21° C. base temperature at root level is required to produce roots on the cuttings.

*Facilities for rooting.*—Mist propagation unit is required for satisfactory rooting of cuttings.

*Crop time* (*from planting a rooted cutting*).—3 months starting in the Spring and 6 months starting in the Fall.

*Plant stem.*—Shape: Cylindrical. Stem dimension: 6 cm in length and 2 mm in diameter. Stem surface: Glabrous and glaucous. Stem color: 145C. Branching: Numerous shoots from the axils of the lower leaves.

*Leaf.*—Type: Evergreen. Shape: Linear, straight. Division: Simple. Apex: Acute. Base: Decurrent. Venation: Not prominent. Margins: Entire. Attachment: Sheathing. Arrangement: Opposite and spiraling up stem. Surfaces (adaxial and abaxial): Glaucous. Stipules: Absent. Fragrance: Absent. Leaf dimensions: 4 to 5 cm in length and 4 mm in width. Leaf color (adaxial and abaxial surfaces): Ranges from 189A to 189B.

*Flower stem.*—Shape: Cylindrical. Dimensions: 13 cm in length (from top of the flower to lower of the 3rd internode), 1.5 mm in width. Color: 188A. Surface: Glabrous and glaucous. Strength: Stiff.

Pedicel:

*Shape.*—Cylindrical.

*Dimensions* (*including calyx*).—25 mm in length and 35 mm in diameter.

*Color.*—188A.

*Surface.*—Glabrous and glaucous.

*Strength.*—Stiff.

Inflorescence:

*Inflorescence type.*—Cymose.

*Number of flowers per stem.*—1-4.

*Flower type.*—Salviform and symmetrical.

*Flower shape.*—Circular.

*Flower profile.*—Reflexed.

*Lastingness.*—10 days at 20° C., on the plant.

*Fragrance.*—Moderate, floral.

*Flowering period.*—Mid-April to October in Devon, UK.

*Bud* (*when first cracking color*).—Shape: Cylindrical. Dimensions: 18 mm in length and 5 mm in width. Color: N138C and N138D towards apex, 139D towards base. Anthocyanin: Absent.

*Corolla.*—Profile: Flat. Petal arrangement: Persistent, apopetalous, and slightly overlapping. Petal margin: Crenate-dentate. Indentations: Depth varies between 1 mm and 3 mm. Petal texture: Soft. Flower type: Single. Petal number: 5. Dimensions: 38 mm in length, 20 mm in width. Petal shape: Obdeltoid consisting of rounded blade and tapering strap. Petal surface: Smooth, except base lightly pubescent. Petal apex: Rounded. Petal base: Truncate, petal tapers towards base. Petal color pattern: Symmetrical picotee; pairs of light pink "blotches" within dark magenta background. Color of adaxial surface (petal newly-opened): Blade ground: Ranges between 59A and 61A. Blade blotches: 73A. Strap: Ranges between 145C and 145D. Color of abaxial surface (petal newly-opened): Blade: White but translucent such that colors of adaxial surface are visible. Strap: Ranges between 145C and 145D.

*Calyx.*—Calyx shape: Cylindrical. Calyx dimensions: 19 mm in depth and 5 mm in diameter. Number of sepals: 5, fused to 3 mm below apex. Sepal apex: Acuminate. Sepal base: Cuneate. Sepal dimensions: 19 mm in length and 4 mm in width. Color of sepals, adaxial surface: 137B and 137C, fading to 144A at base. Color of sepals, abaxial surface: 145B. Anthocyanin: Present at apex and occasionally on sepal base. Splitting: Not observed.

*Epicalyx.*—Bracts: 1 pair of 2. Bracts shape: Acuminate. Bracts dimensions: 10 mm in length and 5 mm in width. Bracts color: Range between 133A and 133C. Anthocyanin: Absent.

*Bracteoles.*—Number: 1 pair of 2. Dimensions: 10 mm in length and 8 mm in width. Shape: Acute. Color: Range between 133A and 133C. Anthocyanin: Absent.

*Reproductive organs.*—Stamens: Number: 10. Dimensions: 25 mm length and 0.5 mm diameter.

*Color of filaments.*—White.

*Anther number.*—10.

*Anther dimensions.*—1 mm length and 0.5 mm in diameter.

*Color of anthers.*—76A.

*Anther attachment.*—Dorsifixed.

*Pollen.*—Present.

*Style number.*—2.

*Style color.*—White.

*Style dimensions* (*including stigma*).—25 mm in length and 1 mm in diameter.

*Stigma dimensions.*—10 mm in length, bifid, reflexed.

*Stigma color.*—71A.

*Ovary position.*—Superior.

*Ovary dimensions.*—7-8 mm in length and 3-4 mm in diameter.

*Ovary shape.*—Spindle.

*Ovary color.*—145B and 145C.

Seed:

*Number.*—50-100.

*Dimensions.*—3 mm in length and 2 mm in width.

*Color.*—202A.

*Shape.*—Oval and flattened.

*Surface.*—Crinkled.

It is claimed:

1. A new and distinct cultivar of *Dianthus* plant named 'WP11 TYR04' as described and illustrated herein.

* * * * *